United States Patent
Holdmann et al.

(10) Patent No.: US 12,293,839 B2
(45) Date of Patent: May 6, 2025

(54) CANDIDATE SCREENING FOR A TARGET THERAPY

(71) Applicant: St. Jude Medical, Cardiology Division, Inc., St. Paul, MN (US)

(72) Inventors: Lars Holdmann, Wettenberg (DE); Jannis Radeleff, Frankfurt (DE)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 311 days.

(21) Appl. No.: 17/857,847

(22) Filed: Jul. 5, 2022

(65) Prior Publication Data

US 2024/0006073 A1    Jan. 4, 2024

(30) Foreign Application Priority Data

Jun. 29, 2022    (DE) .................. 10 2022 116 219.2

(51) Int. Cl.
*G16H 50/30* (2018.01)
*G16H 15/00* (2018.01)
*G16H 50/70* (2018.01)

(52) U.S. Cl.
CPC ............. *G16H 50/30* (2018.01); *G16H 15/00* (2018.01); *G16H 50/70* (2018.01)

(58) Field of Classification Search
CPC ......... G16H 50/30; G16H 15/00; G16H 50/70
See application file for complete search history.

(56) References Cited

U.S. PATENT DOCUMENTS

| | | | |
|---|---|---|---|
| 2007/0203761 A1* | 8/2007 | Keen et al. | |
| 2010/0169218 A1* | 7/2010 | Wang et al. | |
| 2014/0249835 A1 | 9/2014 | Byrom | |
| 2015/0039344 A1* | 2/2015 | Kinney et al. | |
| 2015/0178874 A1* | 6/2015 | Harris et al. | |
| 2016/0034986 A1* | 2/2016 | Ortiz | |
| 2017/0235887 A1* | 8/2017 | Cox et al. | |
| 2017/0344709 A1* | 11/2017 | Dey et al. | |

(Continued)

FOREIGN PATENT DOCUMENTS

| | | |
|---|---|---|
| WO | 2015187154 | 12/2015 |
| WO | 2019168956 | 9/2019 |

OTHER PUBLICATIONS

Consulting Contract, dated May 30, 2022.

(Continued)

*Primary Examiner* — Jonathan Ng
*Assistant Examiner* — William T. Monticello
(74) *Attorney, Agent, or Firm* — SLEMAN & LUND LLP (57) ABSTRACT

Techniques are provided for candidate screening for a target therapy. A plurality of medical codes corresponding to patient billing data are identified. A candidate classification model for a target therapy is generated by selecting a set of medical codes from the plurality of medical codes and assigning a weight to each medical code selected. The candidate classification model is applied to patient billing data for a plurality of patients to generate a set of target therapy scores. The patient billing data includes associations between one or more patients of the plurality of patients and one or more medical codes of the plurality of medical codes. Each target therapy score corresponds to a patient of the plurality of patients, and is calculated based on weights for one or more medical codes associated with the patient.

9 Claims, 4 Drawing Sheets

(56) References Cited

U.S. PATENT DOCUMENTS

2018/0374844 A1* 12/2018 Nishida et al.
2019/0125362 A1*  5/2019 Tischler
2020/0027531 A1   1/2020 White
2020/0035360 A1   1/2020 Vest
2020/0226321 A1*  7/2020 Burns et al.
2021/0085330 A1*  3/2021 Sauer
2022/0044826 A1*  2/2022 Schaeffer et al.
2022/0084633 A1*  3/2022 Das et al.
2022/0319643 A1* 10/2022 Skees et al.
2023/0071973 A1*  3/2023 Freedholm et al.

OTHER PUBLICATIONS

Holmes, David R., et al. "Left atrial appendage occlusion: opportunities and challenges." Journal of the American College of Cardiology 63.4 (2014): 291-298.

* cited by examiner

CANDIDATE SCREENING FOR A TARGET THERAPY

CROSS-REFERENCE TO RELATED APPLICATIONS

This application claims the benefit of the filing date of DE Patent Application No. 10 2022 116 219.2, filed Jun. 29, 2022, the disclosure of which is hereby incorporated by reference herein.

FIELD OF THE DISCLOSURE

The present disclosure relates generally to systems and methods for analyzing standardized administrative data to identify potential candidates for a target therapy.

BACKGROUND

Hospitals and clinicians often face the challenge of identifying suitable treatments for a patient. Hospitals and other medical organizations often manage patient medical data using large clinical information systems (CIS) that collect and store patient information generated in the course of treatment. While a CIS may manage a large amount of data, the data may not be easily accessed across departments. Furthermore, the data generated by different care providers, departments, and medical organizations may be inconsistent in content and format, causing challenges in accessing, interpreting, or analyzing the data across care providers, departments, or medical organizations. Furthermore, laws, regulations, standards, and other rules may restrict the sharing of patient information. Care providers are not able to easily access each piece of relevant data managed by a medical organization to determine treatment options for the patient. A care provider may fail to identify a candidate patient for a target therapy due to the lack of accessible information.

Accordingly, it would be advantageous to access available data, in a manner that is consistent with applicable laws, regulations, standards, or other rules, to identify patients for specific treatment options.

SUMMARY

The appended claims may serve as a summary.

DETAILED DESCRIPTION

In the following description, numerous specific details are set forth in order to provide a thorough understanding of the disclosure. It will be apparent, however, that the embodiments may be practiced without these specific details. The detailed description that follows describes exemplary embodiments and the features disclosed are not intended to be limited to the expressly disclosed combination(s). Therefore, unless otherwise noted, features disclosed herein may be combined to form additional combinations that were not otherwise shown for purposes of brevity.

It will be further understood that: the term "or" may be inclusive or exclusive unless expressly stated otherwise; the term "set" may comprise zero, one, or two or more elements; the terms "first", "second", "certain", and "particular" are used as naming conventions to distinguish elements from each other, and does not imply an ordering, timing, or any other characteristic of the referenced items unless otherwise specified; the term "and/or" as used herein refers to and encompasses any and all possible combinations of one or more of the associated listed items; that the terms "comprises" and/or "comprising" specify the presence of stated features, but do not preclude the presence or addition of one or more other features.

A "computer system" refers to one or more computers, such as one or more physical computers, virtual computers, and/or computing devices. For example, a computer system may be, or may include, one or more server computers, desktop computers, laptop computers, mobile devices, special-purpose computing devices with a processor, cloud-based computers, cloud-based cluster of computers, virtual machine instances, and/or other computing devices. A computer system may include another computer system, and a computing device may belong to two or more computer systems. Any reference to a "computer system" may mean one or more computers, unless expressly stated otherwise. When a computer system performs an action, the action is performed by one or more computers of the computer system.

A "device" may be a computer system, hardware, and/or software stored in, or coupled to, a memory and/or one or more processors on one or more computers. As an alternative or addition, a device may comprise specialized circuitry. For example, a device may be hardwired or persistently programmed to support a set of instructions to perform the functions discussed herein. A device may be a standalone component, work in conjunction with one or more other devices, contain one or more other devices, and/or belong to one or more other devices.

A "component" may be hardware and/or software stored in, or coupled to, a memory and/or one or more processors on one or more computers. As an alternative or addition, a component may comprise specialized circuitry. For example, a component may be hardwired and/or persistently programmed with a set of instructions to perform the functions discussed herein. A component may be a standalone component, work in conjunction with one or more other components, contain one or more other components, and/or belong to one or more other components.

General Overview

The present disclosure generally describes techniques for candidate screening for a target therapy by generating a candidate classification model and applying the candidate classification model to patient billing data. Patient billing data is a form of hospital data that is typically standardized to ensure that medical billing is performed accurately and consistently. For example, insurance companies and government entities often require the use of a standardized coding system for medical services and procedures. The candidate classification model is configured based on a set of medical codes that are correlated to the target therapy. For example, the candidate classification model may model inclusion criteria and/or exclusion criteria for the target therapy using selected medical codes. The candidate classification model is applied to a set of patient billing data to identify candidate patients that would potentially benefit from the target therapy. For example, a medical organization may submit a set of data representing a set of patients to screen the set of patients. A care provider for a candidate patient may further evaluate the candidate patient based on the results of the screening. Data and privacy protection techniques may be implemented to manage compliance with privacy and authorization requirements. For example, pseudonymization may be applied to protect the privacy of the set of patients during the screening process.

One aspect of the disclosure is directed to a computer system including one or more hardware processors and at least one memory storing one or more instructions. The instructions, when executed by the one or more hardware processors, cause the one or more hardware processors to identify a plurality of medical codes corresponding to patient billing data; generate a candidate classification model for a target therapy by selecting a set of medical codes from the plurality of medical codes and assigning a weight to each medical code selected; receive patient billing data for a plurality of patients, the patient billing data including associations between one or more patients of the plurality of patients and one or more medical codes of the plurality of medical codes; apply the candidate classification model to the patient billing data to generate a set of target therapy scores, each target therapy score of the set of target therapy scores corresponding to a patient of the plurality of patients and calculated based on weights for one or more medical codes associated with the patient; and provide target therapy candidate data generated based on the set of target therapy scores.

In some examples, the target therapy candidate data identifies one or more candidate patients having a target therapy score that meets a target therapy score threshold.

In some examples, the target therapy candidate data includes an individual report for at least one patient of the plurality of patients.

In some examples, the target therapy candidate data includes aggregate data for one or more target therapy classifications over one or more groupings of the plurality of patients.

In some examples, receiving the patient billing data includes receiving the patient billing data from a medical organization. As an alternative or addition, providing the target therapy candidate data may include providing the set of target therapy scores to the medical organization.

In some examples, the patient billing data is received in a deidentified form. As an alternative or addition, the target therapy candidate data may reference individual patients in the plurality of patients by pseudonym.

In some examples, generating the candidate classification model for the target therapy includes assigning one or more negative weights to one or more medical codes corresponding to one or more exclusion criteria for the target therapy, and assigning one or more positive weights to one or more medical codes corresponding to one or more inclusion criteria for the target therapy.

In some examples, the instructions, when executed by the one or more hardware processors, cause the one or more hardware processors to provide a user interface for adjusting one or more weights assigned to one or more medical codes of the set of medical codes.

In some examples, generating the candidate classification model includes using machine learning techniques to assign one or more weights of the candidate classification model based on a training data set comprising: input data comprising associations between medical codes and a plurality of sample patients; and output data comprising a sample target therapy score for each sample patient of the plurality of sample patients.

In some examples, the instructions, when executed by the one or more hardware processors, cause the one or more hardware processors to receive care provider review data corresponding to one or more target therapy scores of the set of target therapy scores, and update the candidate classification model by adjusting one or more weights assigned to one or more medical codes of the set of medical codes based on the care provider review data.

In some examples, the instructions, when executed by the one or more hardware processors, cause the one or more hardware processors to identify, in the patient billing data, one or more unprocessed medical codes not in the plurality of medical codes, and update the candidate classification model by selecting one or more unprocessed medical codes from the one or more unprocessed medical codes and assigning a weight to each unprocessed medical code selected.

In some examples, generating the candidate classification model includes grouping two or more medical codes in the set of medical codes into a code group, and assigning a single weight to the code group to indirectly assign weights to the two or more medical codes of the code group.

In some examples, the target therapy is a left atrial appendage (LAA) occlusion comprising an LAA occluder implantation procedure.

One aspect of the disclosure is directed to a method that includes identifying a plurality of medical codes corresponding to patient billing data; generating a candidate classification model for a target therapy by selecting a set of medical codes from the plurality of medical codes and assigning a weight to each medical code selected; receiving patient billing data for a plurality of patients, the patient billing data including associations between one or more patients of the plurality of patients and one or more medical codes of the plurality of medical codes; applying the candidate classification model to the patient billing data to generate a set of target therapy scores, each target therapy score of the set of target therapy scores corresponding to a patient of the plurality of patients and calculated based on weights for one or more medical codes associated with the patient; and providing target therapy candidate data generated based on the set of target therapy scores; wherein the method is performed by one or more processors.

In some examples, receiving the patient billing data includes receiving the patient billing data from a medical organization. As an alternative or addition, providing the target therapy candidate data set includes providing the set of target therapy scores to the medical organization. As an alternative or addition, the patient billing data is received from the medical organization in a deidentified form. As an alternative or addition, the target therapy candidate data references individual patients in the plurality of patients by pseudonym.

In some examples, generating the candidate classification model includes using machine learning techniques to assign one or more weights of the candidate classification model based on a training data set comprising: input data comprising associations between medical codes and a plurality of sample patients; and output data comprising a sample target therapy score for each sample patient of the plurality of sample patients.

In some examples, the method further includes receiving care provider review data corresponding to one or more target therapy scores of the set of target therapy scores, and updating the candidate classification model by adjusting one or more weights assigned to the one or more medical codes of the set of medical codes based on the care provider review data.

One aspect of the disclosure is directed to a non-transitory computer-readable medium storing instructions. The instructions, when executed by one or more processors of a network system, cause the network system to identify a plurality of medical codes corresponding to patient billing data; generate a candidate classification model for a target therapy by selecting a set of medical codes from the plurality of medical codes and assigning a weight to each medical code selected; receive patient billing data for a plurality of patients, the patient billing data including associations between one or more patients of the plurality of patients and one or more medical codes of the plurality of medical codes; apply the candidate classification model to the patient billing data to generate a set of target therapy scores, each target therapy score of the set of target therapy scores corresponding to a patient of the plurality of patients and calculated based on weights for one or more medical codes associated with the patient; and provide target therapy candidate data generated based on the set of target therapy scores.

In some implementations, the various techniques described herein may achieve one or more of the following advantages: screening for a target therapy is efficiently performed in a scalable manner; patient billing data from multiple sources is converted into usable data that enables medical organizations and care providers to improve patient care; patient outcomes are potentially improved; the candidate classification model may be updated based on additional data and/or research; data processing and analysis is standardized and streamlined; compliance with laws and regulations regarding privacy and health is enforced; generation of statistical data allows for study of population trends; a medical organization may use statistical data regarding a patient population to make budgeting, staff, infrastructure, and other spending decisions; and a candidate classification model for a target therapy may be iteratively improved based on care provider review, target therapy treatment outcomes, or other additional data. Additional features and advantages are apparent from the specification and the drawings.

System Overview

Figure 1:
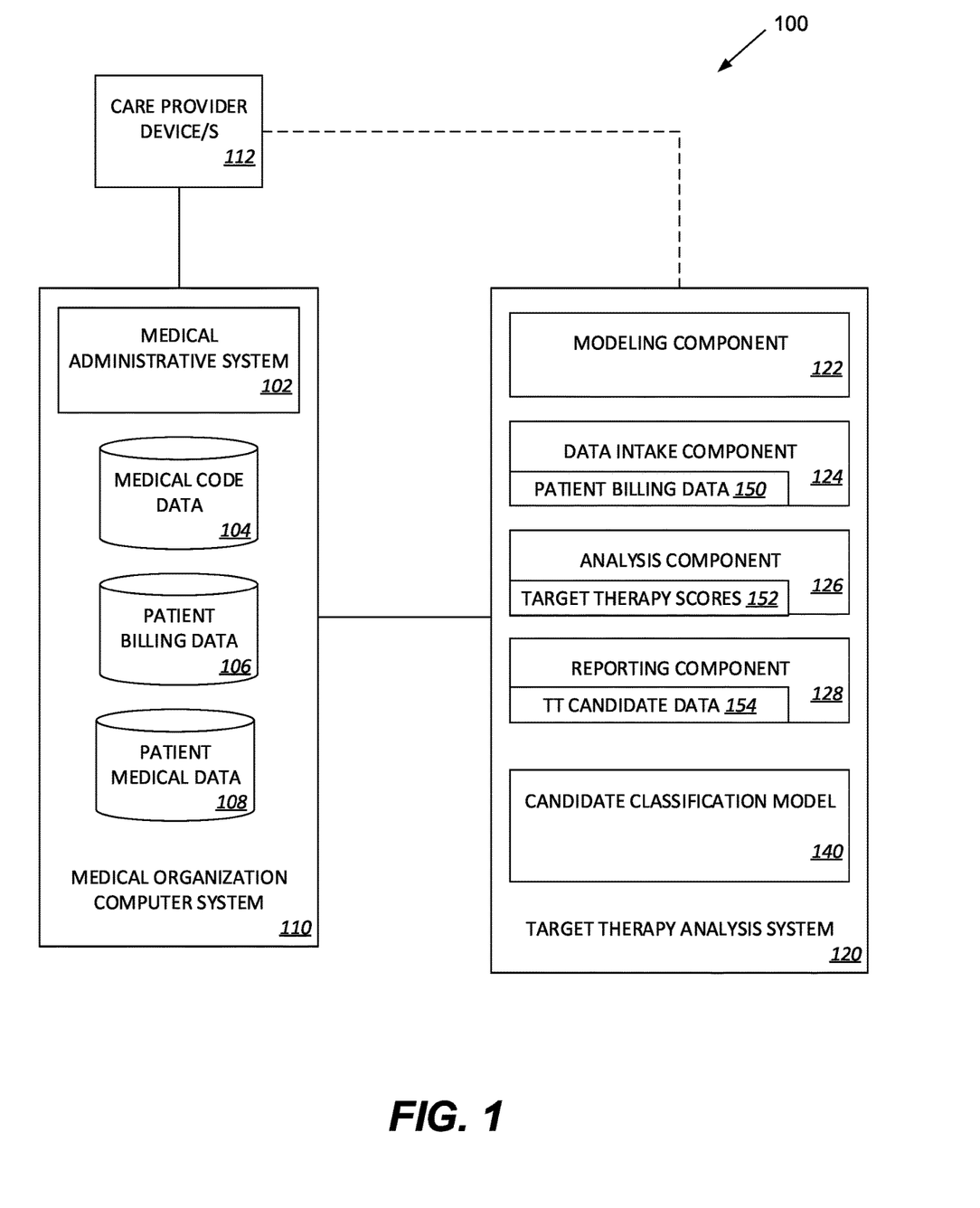
FIG. 1 illustrates a block diagram of an example computer system in accordance with an aspect of the disclosure.

FIG. 1 illustrates a block diagram of an example computer system in accordance with an aspect of the disclosure. The computer system 100 includes a target therapy analysis system 120, a medical organization computer system 110, and one or more care provider devices 112. The target therapy analysis system 120 and the medical organization computer system 110 may communicate over one or more networks. The network/s may include one or more local area networks (LANs) and/or one or more wide area networks, such as the Internet.

The medical organization computer system 110 includes one or more computers and/or devices that are owned and/or controlled by a medical organization. A medical organization is an entity that provides health care services, such as a hospital, clinic, office, group, or other entity that provides health care services. A medical organization may include a group of medical organizations. The medical organization computer system 110 stores patient information generated in the course of providing treatment to patients of the medical organization. In some examples, the medical organization computer system 110 includes a clinical information system (CIS) that manages clinical data.

A medical organization may include one or more care providers, such as doctors, nurses, therapists, technicians, and/or other health care professionals. A care provider is an individual who may generate patient data in the course of providing treatment to patients of the medical organization. A care provider may operate one or more care provider devices 112 to enter patient data. While the care provider device/s 112 are illustrated as distinct from the medical organization computer system 110, they may include computing devices that are part of the medical organization computer system 110, such as devices that are owned by the corresponding medical organization. As an alternative or addition, one or more care provider devices 112 may be devices that are owned and/or controlled by one or more care providers.

The medical organization computer system 110 includes a medical administrative system 102. The medical administrative system 102 manages aspects of the medical billing process, such as itemizing health care services provided to patients, maintaining rates for health care services, insurance submissions, invoicing, payments, and/or other aspects of medical billing.

The medical organization computer system 110 may maintain medical code data 104. The medical code data 104 may include medical codes that are organized in a standardized coding system. For example, the World Health Organization (WHO) maintains the International Classification of Diseases (ICD), a standardized system of diagnosis codes that represent conditions and diseases, related health problems, abnormal findings, signs and symptoms, injuries, external causes of injuries and diseases, and/or social circumstances. The ICD includes different editions (e.g., ICD-10, ICD-11). Many countries use modifications of the ICD that are tailored to their health system infrastructure, such as the ICD-10-CM & ICD-10-PCD the United States, the ICD-10-GM in Germany, and the ICD-10-FR in France. Other standardized coding systems may be used, such as the Operationen- and Prozedurenschlüssel (OPS) in Germany and the Classification Commune des Actes Médicaux (CCAM) in France.

The medical administrative system 102 uses the medical code data 104 to manage billing for health care services provided to patients, such as physical examinations, tests, imaging, other diagnostic procedures, facilities, surgical procedures, therapeutic procedures, rehabilitative procedures, other procedures, medications, devices, therapies, and/or other medical services or items provided by the medical organization. In some examples, the medical administrative system 102 uses the medical codes of the medical code data 104 as billing codes. As an alternative or addition, the medical administrative system 102 may use one or more custom billing codes that are each linked to one or more medical codes of the medical code data 104.

The medical organization computer system 110 may store patient data, such as patient billing data 106 and patient medical data 108. The patient billing data 106 includes associations between one or more patients of the medical organization and one or more medical codes. For example, when a care provider submits a report indicating that a particular patient received a particular treatment for a particular diagnosis from a care provider device 112, the medical administrative system 102 may use the medical code data 104 to generate and store patient billing data 106 associating the particular patient with one or more medical codes corresponding to the treatment and/or diagnosis. For example, the medical administrative system 102 may create patient billing data 106 that directly includes one or more corresponding medical codes from the medical code data 104. As an alternative or addition, the patient billing data 106 may include one or more custom billing codes that are linked to one or more corresponding medical codes from the medical code data 104.

In some examples, the medical organization computer system 110 stores patient medical data 108. In the example above, the patient medical data 108 for the particular patient may include the report submitted by the care provider, care provider notes on the particular patient's diagnosis or treatment, health data collected during one or more visits by the particular patient, the particular patient's medical history, the particular patient's personal information, and/or other medical information corresponding to the particular patient.

The target therapy analysis system 120 performs candidate screening for a target therapy. For example, the target therapy may include therapeutic procedures, surgical procedures, testing, clinical trials, patient registries, diagnostic procedures, or any other procedure that may be performed in the course of medical treatment. In some examples, the target therapy includes procedures and/or medical devices related to repairing heart defects, heart valve replacement and repair, such as cardiac rhythm management, electrophysiology, valve repair, valve replacement, and other procedures and/or medical devices. An example target therapy analysis system that performs candidate screening for left atrial appendage (LAA) occlusion is described in greater detail hereinafter.

The target therapy analysis system 120 includes a modeling component 122. The modeling component 122 of the target therapy analysis system 120 generates a candidate classification model 140. The candidate classification model 140 is used to perform candidate screening for a target therapy, such as by applying the candidate classification model 140 to patient billing data 150 for a plurality of patients to generate target therapy scores 152 for one or more patients. A target therapy score 152 quantifies a particular patient's suitability as a candidate for the target therapy.

The modeling component 122 generates the candidate classification model 140 for the target therapy based on a set of medical codes. The set of medical codes are selected from a plurality of medical codes corresponding to patient billing data. For example, the medical codes may include medical codes that are organized in a standardized coding system. The plurality of medical codes may include the medical codes stored in the medical code data 104 of the medical organization computer system 110. In some examples, the plurality of medical codes used by the modeling component 122 includes medical codes from a plurality of standardized coding systems to ensure compatibility with a plurality of medical organization computer systems 110.

The modeling component 122 selects the set of medical codes to use in the candidate classification model 140 and assigns a weight to each medical code selected. A weight that is assigned to a particular medical code indicates the contribution of the particular medical code in determining a target therapy score 152 for a patient when the patient billing data 150 associates the patient with the particular medical code. A medical code associated with a patient in the patient billing data 150 may correspond to conditions and diseases, related health problems, abnormal findings, signs and symptoms, injuries, external causes of injuries and diseases, and/or social circumstances.

The target therapy analysis system 120 includes a data intake component 124. The data intake component 124 of the target therapy analysis system 120 intakes patient billing data 150 for a plurality of patients. For example, the data intake component 124 may receive patient billing data 150 from the medical organization computer system 110. The patient billing data includes associations between one or more patients of the plurality of patients and one or more medical codes. In some examples, the data intake component 124 performs consistency checks on the received patient billing data 150 to ensure that the patient billing data 150 is in the proper form for applying the candidate classification model 140.

In some examples, the medical organization computer system 110 generates the patient billing data 150 received by the target therapy analysis system 120 based on the patient billing data 106 stored by the medical organization computer system 110. For example, the medical organization computer system 110 may select a subset of patient billing data 106 corresponding to particular patients, such as patients in a particular department, patients in a specific demographic group, or another subset of patients. As an alternative or addition, the medical organization computer system 110 may select a subset of patient billing data corresponding to a relevant time period for analysis using the candidate classification model 140.

In some examples, the medical organization computer system 110 may generate the patient billing data 150 received by the target therapy analysis system 120 by processing the patient billing data 106 to ensure compliance with one or more laws or regulations regarding data protection. In some examples, the data intake component 124 receives the patient billing data 106 in a deidentified form. For example, the medical organization computer system 110 may ensure that the patient billing data 150 transmitted to the target therapy analysis system 120 only includes routine administrative data that is pseudonymized. The medical organization computer system 110 may create pseudonymized patient billing data 150 based on its patient billing data 106 and send the pseudonymized patient billing data 150 to the target therapy analysis system 120.

In some examples, the medical organization computer system 110 may retain information that allows the medical organization computer system 110 to reidentify target therapy candidate data 154 received from the target therapy analysis system 120. For example, the reporting component 128 of the target therapy analysis system 120 may provide target therapy candidate data 154 that references individual patients by pseudonym, allowing the medical organization computer system 110 to reidentify the individual patients, enabling care providers of the medical organization to provide medical care to the individual patients based on the target therapy candidate data 154. The identity and personal data of the patients are protected from disclosure outside of the medical organization, and the target therapy analysis system 120 only possesses and processes routine administrative data that is pseudonymized.

In some examples, the data intake component 124 identifies one or more unprocessed medical codes that appear in the patient billing data 150 but were not considered by the modeling component 122 to generate the candidate classification model 140. The unprocessed medical codes may be used to further improve the candidate classification model 140, as described in one or more examples in greater detail hereinafter.

The target therapy analysis system 120 includes an analysis component 126. The analysis component 126 of the target therapy analysis system 120 applies the candidate classification model 140 to the patient billing data 150 to generate a set of target therapy scores 152. Each target therapy score 152 quantifies the suitability of a patient as a candidate for the target therapy. When the candidate classification model 140 is applied to patient billing data 150, a target therapy score 152 is generated for one or more patients based on weights of the candidate classification model 140 for one or more medical codes associated with each patient in the patient billing data 150. The target therapy score 152 may include one or multiple components. For example, applying the candidate classification model 140 to patient billing data 150 may cause the candidate classification model 140 to generate a single output score for each patient of the patients represented in the patient billing data 150. As an alternative or addition, the candidate classification model 140 may generate a single output score for a subset of patients represented in the patient billing data 150. As an alternative or addition, the candidate classification model 140 may generate multiple output scores for one or more patients represented in the patient billing data 150, each output score representing an aspect of the patient's suitability as a candidate for the target therapy. The target therapy score may be a probability, a boolean, an integer, a decimal number, a classification, or any other value that can describe suitability for the target therapy.

The target therapy analysis system 120 includes a reporting component 128. The reporting component 128 of the target therapy analysis system 120 provides target therapy candidate data 154 in a reporting format. In some examples, the target therapy candidate data 154 includes one or more target therapy scores 152 output by the candidate classification model 140. As an alternative or addition, the target therapy candidate data 154 may be generated by further processing the target therapy scores 152. For example, the target therapy candidate data 154 may include data that classifies one or more patients based on the target therapy score, such as but not limited to the following example sets of target therapy classifications: {"HIGH RISK", "MEDIUM RISK", "LOW RISK"}, and/or {"CANDIDATE", "NO INDICATION"}. In some examples, the medical organization may specify the parameters for one or more target therapy classifications used in the target therapy candidate data 154.

In some examples, the target therapy candidate data 154 is provided to an operator of the target therapy analysis system 120. As an alternative or addition, the target therapy candidate data 154 may be provided to the medical organization computer system 110. As an alternative or addition, the target therapy candidate data 154 may be provided to a care provider device 112 of a care provider belonging to the medical organization. In some examples, the target therapy candidate data 154 is secured, such as by encryption and/or password protection. As an alternative or addition, the target therapy candidate data 154 may reference individual patients by pseudonym. The medical organization computer system 110 may use reidentification data generated when preparing the patient billing data 150 to reidentify individual patients referenced by pseudonym in the target therapy candidate data 154.

The reporting component 128 may generate the target therapy candidate data 154 in the form of one or more files. For example, the file/s may include one or more of a spreadsheet, a text document, a Portable Document Format (PDF) document, an image, a HyperText Markup Language (HTML) document, another web-format document, a file having a proprietary format, or any other file. In some examples, the reporting component 128 provides a graphical user interface for display on a computing device operated by a user for the user to access the target therapy candidate data 154. The graphical user interface may allow the user to manipulate the target therapy candidate data 154, such as by selecting reporting parameters for the presentation of the target therapy candidate data 154.

In some examples, the target therapy candidate data 154 includes data for all patients represented in the patient billing data 150. As an alternative or addition, the target therapy candidate data 154 may include data for a subset of the patients represented in the patient billing data 150. For example, the target therapy candidate data 154 may identify one or more candidate patients having a target therapy score that meets a target therapy score threshold. When a patient's target therapy score is above the target therapy score threshold, a care provider may further evaluate the patient as a potential candidate for the target therapy. As an alternative or addition, the target therapy candidate data 154 may include an individual report for at least one patient. The individual report may include additional information about the corresponding patient, such as one or more additional medical scores generated based on the patient billing data 150, one or more medical codes associated with the patient in the patient billing data 150, or other information. In some examples, the individual report is provided to a care provider that has provided medical care to the patient.

In some examples, the target therapy candidate data 154 includes aggregate data for one or more target therapy classifications over one or more groupings of the plurality of patients. The aggregate data may include one or more of a count, a percentage, average, minimum, maximum, average, or other aggregate data. In some examples, the reporting component 128: (1) groups the patients represented in the patient billing data based on a first factor, such as a department, a demographic group, and/or the association of a particular medical code to the group of patients; (2) classifies the patients by target therapy classification based on the target therapy score associated with each classified patient; and (3) generates aggregate data for each grouping and target therapy classification. Tables 1-3 are examples of aggregate data generated by the reporting component 128.

TABLE 1

Aggregate Data: Count of Patients by Age Group and Target Therapy Classification

| Age Group | CANDIDATE | NO INDICATION |
|---|---|---|
| 0-39 | 0 | 1 |
| 40-49 | 9 | 1436 |
| 50-59 | 16 | 1503 |
| 60-69 | 15 | 1423 |
| 70-79 | 12 | 1208 |
| 80+ | 2 | 1193 |

TABLE 2

Aggregate Data: Percent of Patients Classified as CANDIDATE, by Department

| Department | % CANDIDATE |
|---|---|
| Cardiology | 5.2% |
| Geriatrics | 3.6% |
| Endocrinology | 1.2% |

TABLE 2-continued

Aggregate Data: Percent of Patients Classified as CANDIDATE, by Department

| Department | % CANDIDATE |
|---|---|
| Internal Medicine | 0.3% |
| Nephrology | 0.8% |
| Pediatrics | 0.1% |

TABLE 3

Aggregate data: Average Age of Patients Classified as CANDIDATE, by Department

| Department | Age |
|---|---|
| Cardiology | 42.3 y |
| Geriatrics | 67.8 y |
| Endocrinology | 55.4 y |
| Internal Medicine | 54.2 y |
| Nephrology | 49.5 y |
| Pediatrics | 11.0 y |

The target therapy analysis system 120 and/or its components (e.g. modeling component 122, data intake component 124, analysis component 126 and/or reporting component 128) as described herein are presented as individual components for ease of explanation. Any action performed by or to one or more components of the target therapy analysis system 120 may be considered performed by or to the target therapy analysis system 120. The target therapy analysis system 120 and/or its components may be implemented as one or more dependent or independent processes, and may be implemented on one or multiple computers. For example, a component may be implemented as a distributed system. As an alternative or addition, multiple instances of one or more components may be implemented. In some examples, one or more components of the target therapy analysis system 120 may be implemented as a cloud service and/or using one or more cloud service providers. Furthermore, a component may be implemented fully and/or partially in one or multiple programs and/or processes, and two or more components shown may be implemented fully and/or partially in the same program and/or process.

Candidate Classification Model Configuration

In some examples, the modeling component 122 assigns a positive weight to a medical code corresponding to one or more inclusion criteria for the target therapy. The positive weight results in a target therapy score that is higher when a patient is associated with the medical code corresponding to the inclusion criteria. As an alternative or addition, the modeling component 122 may assign one or more negative weights to a medical code corresponding to one or more exclusion criteria for the target therapy. The negative weight results in a target therapy score that is lower when a patient is associated with the medical code corresponding to the exclusion criteria.

In some examples, the modeling component 122 generates the candidate classification model 140 based on time information associated with the patient billing data 106. For example, the modeling component 122 may generate the candidate classification model 140 based on an assumption that the patient billing data 106 includes billing information for medical services provided during a particular time period, such as medical services provided during the preceding year. As an alternative or addition, the modeling component 122 may factor in a date or a time elapsed for one or more medical codes. For example, if performance of a major surgical procedure in the last three months is an exclusion factor for the target therapy, the modeling component 122 may assign a conditional weight to one or more medical codes corresponding to major surgical procedures, where the conditional weight is a calculated to be negative when the time elapsed since a date associated with the medical code is less than three months. A conditional weight may be implemented as a formula applied to time information associated with the medical code in the patient billing data 106.

The medical code data 104 may include a plurality of medical codes arranged in a hierarchical structure. For example, the ICD-10-CM coding scheme includes codes with between three and seven characters that specify a hierarchy. The first three characters designate a category, the next three characters specify etiology, anatomic site, severity, or other vital details, while the last character is primarily used to document episode of care or other conditions. For example, Table 4 includes a set of ICD-10-CM codes that are arranged hierarchically:

TABLE 4

Example ICD-10-CM Codes

| ICD-10-CM Code | Description |
|---|---|
| D30 | Benign neoplasm of urinary organs |
| D30.0 | Benign neoplasm of kidney |
| D30.00 | Benign neoplasm of unspecified kidney |
| D30.01 | Benign neoplasm of right kidney |
| D30.02 | Benign neoplasm of left kidney |

In some examples, the modeling component 122 generates the candidate classification model 140 by grouping two or more medical codes into a code group, and assigns a single weight to the code group to indirectly assign weights to the two or more medical codes of the code group. For example, the modeling component 122 may create a code group corresponding to medical codes beginning with "D30". The code group includes the ICD-10-CM code "D30" and other ICD-10-CM codes that are below the code "D30" in the hierarchical structure of the ICD-10-CM coding scheme, including "D30.0", "D30.00", "D30.01", and "D30.02". The modeling component 122 may assign a weight w to the code group, causing the other ICDM-10 codes that are below the code "D30" to also be associated with the weight w. When patient billing data 106 for a patient is associated with any medical code in the code group, the weight w will be used to calculate the target therapy score for the patient when the candidate classification model 140 is applied.

In some examples, the modeling component 122 allows human input for selecting one or more medical codes and/or generating one or more corresponding weights. For example, the modeling component 122 may take input from a researcher, clinician, or other expert regarding one or more medical codes and/or code groups. In some examples, the modeling component 122 takes human input that specifies one or more weights for one or more medical codes and/or code groups. As an alternative or addition, the modeling component 122 may take human input that is used to modify one or more weights, such as by causing an increase or decrease in one or more weights. In some examples, the modeling component 122 provides a graphical user interface for display on a computing device operated by a user for the user to enter the human input.

As an alternative or addition, the modeling component 122 may use machine learning techniques to generate and/or adjust the candidate classification model 140. For example, the modeling component 122 may use machine learning techniques to generate and/or adjust one or more weights of the candidate classification model 140. In some examples, the modeling component 122 implements machine learning algorithms to generate one or more weights of the candidate classification model 140 based on a training data set. The training data set includes input data comprising associations between medical codes and a plurality of sample patients. The training data set includes output data comprising a sample target therapy score for each sample patient. The sample target therapy score quantifies the corresponding sample patient's suitability for the target therapy. The sample target therapy score may be a probability, a boolean, an integer, a decimal number, a classification, or any other value that can describe a sample patient's suitability for the target therapy.

In some examples, the training data set is generated based on clinical data involving actual patients, such as a care provider's evaluation of an actual patient's suitability for the target treatment. As an alternative or addition, the training data set may be generated based on retrospective outcomes and/or other retrospective data corresponding to one or more actual patients who were given the target therapy or determined not to be a candidate for the target therapy. As an alternative or addition, the training data set may be generated based on clinical trial data. As an alternative or addition, the training data set may include example patient data designed by a researcher, care provider, or other expert. The modeling component 122 may configure the candidate classification model 140 in an automated manner. As an alternative or addition, the modeling component 122 may configure the candidate classification model 140 with the combination of automation and human input.

In some examples, the modeling component 122 uses a validation data set to evaluate the candidate classification model 140 in a refining process. As an alternative or addition, the modeling component 122 may use a test data set to perform a final evaluation of the candidate classification model 140. The validation data set and/or the test data set have the same data types and data structure as the training data set.

In some examples, the modeling component 122 updates the candidate classification model 140 based on care provider review data regarding one or more previously generated target therapy scores 152, such as by adjusting one or more weights of the candidate classification model 140. The care provider review data may include feedback provided by one or more care providers regarding one or more target therapy scores 152 and/or target therapy candidate data 154 for one or more patients. The feedback may include a different decision made by the care provider regarding a patient's suitability for the target therapy, such as a revision of a target therapy score or a reclassification of a target therapy classification assigned to the patient. As an addition or alternative, the care provider review data may be based on retrospective outcomes and/or other retrospective data corresponding to the patient after the patient was given the target therapy or determined not to be a candidate for the target therapy. The modeling component 122 may adjust one or more weights of the candidate classification model 140 based on machine learning techniques, human input, or a combination thereof.

In some examples, the modeling component 122 updates the candidate classification model 140 based on unprocessed medical codes that appear in the patient billing data 150 but were not considered by the modeling component 122 when the candidate classification model 140 was generated. The modeling component 122 may adjust one or more weights of the candidate classification model 140 based on machine learning techniques, human input, or a combination thereof.

Example Target Therapy—LAA Occlusion

An example target therapy analysis system (e.g., target therapy analysis system 120) performs candidate screening for left atrial appendage (LAA) occlusion comprising an LAA occluder implantation procedure. The LAA is a sac in the muscle wall of the left atrium. In patients with atrial fibrillation, blood can collect and form clots in the LAA, creating a risk of those clots embolizing and resulting in a stroke. An LAA occluder is implanted in the LAA to prevent fluid communication between the LAA and the left atrium of the heart. This sealing or occluding of the LAA may be effective to prevent LAA clots from entering systemic circulation, reducing the risk of stroke. Another therapy used to reduce the risk of stroke is the administration of oral anti-coagulants. However, some patients have contraindications for oral anticoagulants. LAA occlusion has emerged as a treatment option for patients with atrial fibrillation who are at moderate to high risk of stroke, particularly for patients with contraindications for oral anticoagulants and/or patients with a high bleed risk.

The target therapy analysis system generates a candidate classification model (e.g., candidate classification model 140) for an LAA occluder implantation procedure. The candidate classification model may include negative weights for medical codes corresponding to contraindications for LAA occlusion. The negative weights lower the target therapy score for a patient associated with the corresponding medical codes. The magnitude of the negative weight may depend on the degree of contraindication. Medical codes corresponding to exclusion criteria may be assigned higher-magnitude negative weights when the presence of the exclusion criteria eliminates the patient as a candidate for LAA occlusion. For example, such exclusion criteria may include death, palliative therapy, motoric function restriction, cognitive impairment, mechanical heart valve implantation, and dementia. Contraindications assigned a lower-magnitude negative weight include alcoholism and liver cirrhosis.

The candidate classification model includes positive weights for medical codes corresponding to inclusion criteria for LAA occlusion. The positive weights increase the target therapy score for a patient when patient billing data associates the patient with the corresponding medical codes. The magnitude of the positive weights reflects the potential effectiveness of LAA occlusion for a candidate patient associated with the corresponding medical code. For example, medical codes corresponding to atrial fibrillation have a higher-magnitude positive weight. Medical codes corresponding to a risk for bleeding, dialysis, renal failure, and anemia may also be assigned positive weights.

The candidate classification model includes code groups for sets of medical codes. For example, the candidate classification model may include a code group for a set of ICD codes beginning with "I61" that correspond to nontraumatic intracerebral hemorrhage, as listed in Table 5. A positive weight for the code group increases a patient's target therapy score for LAA occlusion when the patient billing data associates the patient with the medical codes in the code group corresponding to nontraumatic intracerebral hemorrhage.

TABLE 5

Nontraumatic Intracerebral Hemorrhage Code Group

| ICD Code | Description |
| --- | --- |
| I61 | Nontraumatic intracerebral hemorrhage in hemisphere, subcortical |
| I61.1 | Nontraumatic intracerebral hemorrhage in hemisphere, cortical |
| I61.2 | Nontraumatic intracerebral hemorrhage in hemisphere, unspecified |
| I61.3 | Nontraumatic intracerebral hemorrhage in brain stem |
| I61.4 | Nontraumatic intracerebral hemorrhage in cerebellum |
| I61.5 | Nontraumatic intracerebral hemorrhage, intraventricular |
| I61.6 | Nontraumatic intracerebral hemorrhage, multiple localized |
| I61.8 | Other nontraumatic intracerebral hemorrhage |
| I61.9 | Nontraumatic intracerebral hemorrhage, unspecified |

A medical organization computer system (e.g., medical organization computer system 110) submits pseudonymized patient billing data (e.g., patient billing data 150) to the target therapy analysis system. The candidate classification model is applied to a sample patient billing data set to generate target therapy scores (e.g., target therapy scores 152) for 11526 patients. The target therapy analysis system generates target therapy candidate data (e.g. target therapy candidate data 154) based on the target therapy scores. The target therapy analysis system provides the target therapy candidate data to the medical organization computer system. The target therapy candidate data references individual patients by pseudonym, allowing the medical organization computer system to reidentify the individual patients. The target therapy candidate data constitutes an initial screening that may be further reviewed by a care provider in the course of providing treatment to the patients.

In an example, the target therapy analysis system generates aggregate data for the following target therapy classifications: LAA OCCLUSION (previously received the target therapy), HIGH RISK (candidate with a high target therapy score above a first threshold), MEDIUM RISK (candidate with a target therapy score between the first threshold and a second threshold), LOW RISK (candidate with a target therapy score between the second threshold and a third threshold), and NO INDICATION (non-candidate with a target therapy score below the third threshold). The aggregate data for the sample patient billing data set is presented in Table 6. The aggregate data shows that: 10 patients are classified as LAA OCCLUSION; 18 patients are classified as HIGH RISK (e.g., of stroke or other factors that would benefit from LAA occlusion); 28 patients are classified as MEDIUM RISK; 130 patients are classified as LOW RISK; and 11340 patients are classified as NO INDICATION. A care provider may use the screening result to identify patients to further evaluate for the target therapy.

TABLE 6

Aggregate Data for Sample Patient Billing Data Set

| Target Therapy Classification | Count |
| --- | --- |
| LAA OCCLUSION | 10 |
| HIGH RISK | 18 |
| MEDIUM RISK | 28 |
| LOW RISK | 130 |
| NO INDICATION | 11340 |

Example Processes

Figure 2:
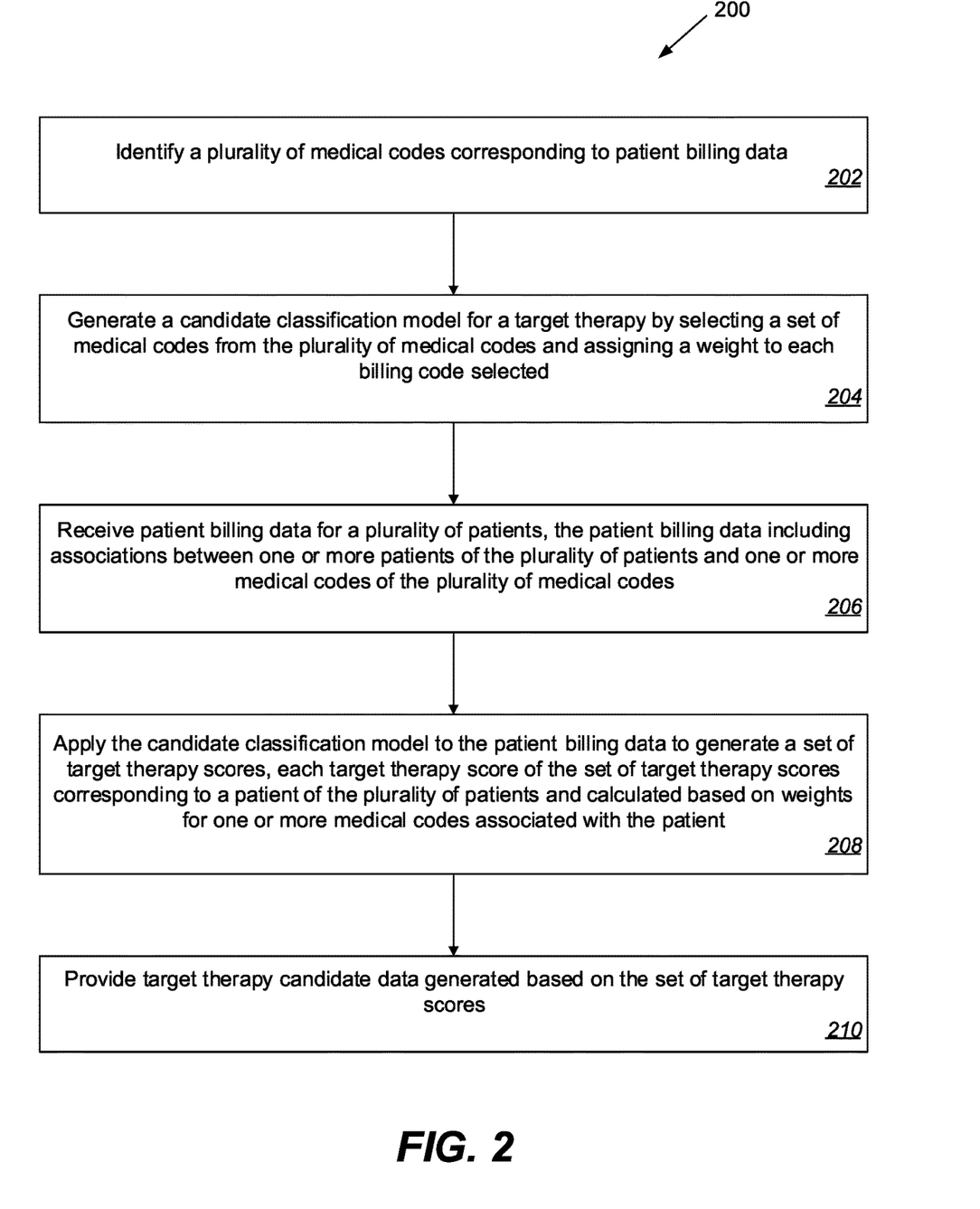
FIG. 2 illustrates a flow diagram of an example process for candidate screening for a target therapy.
Figure 4:
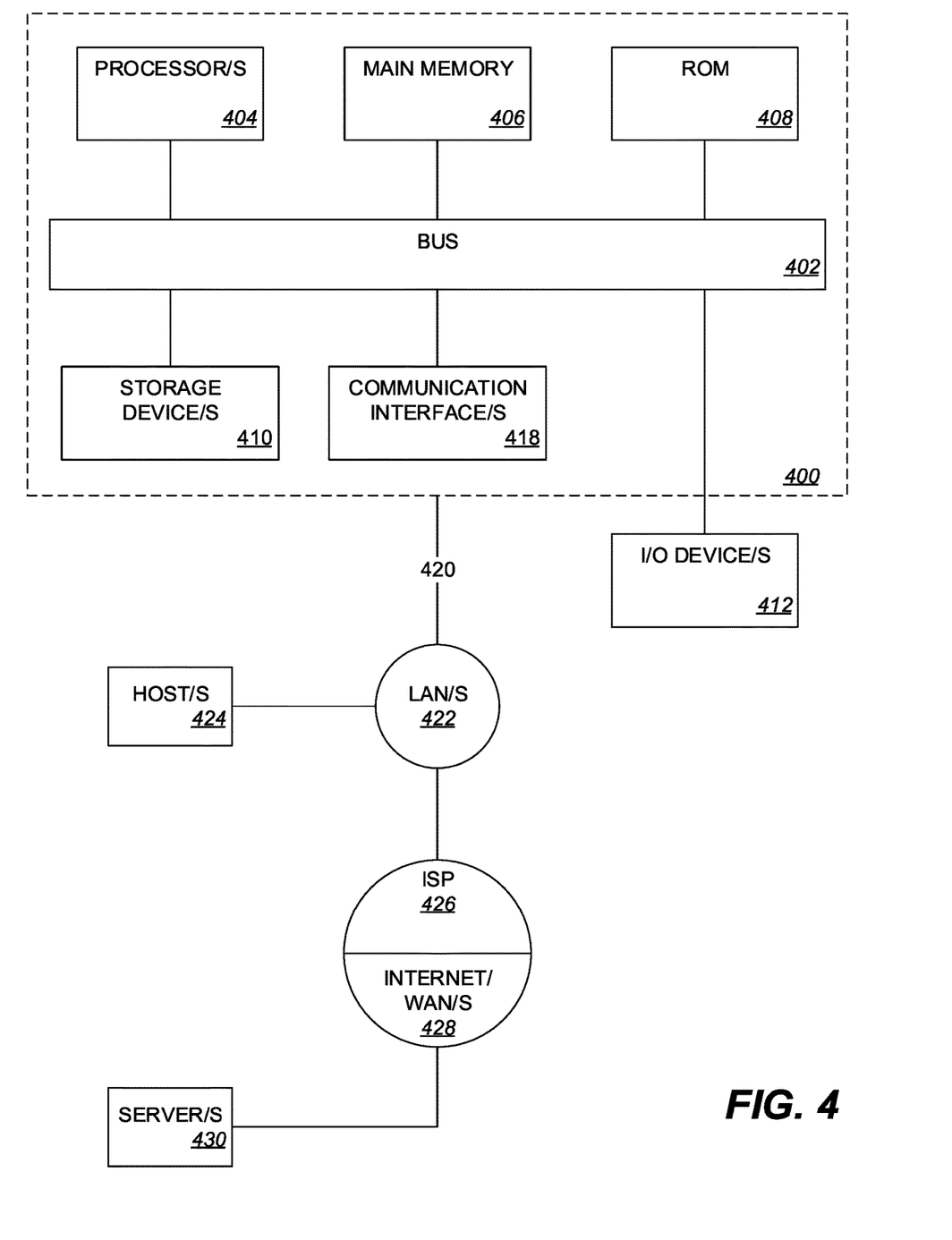
FIG. 4 is a block diagram that illustrates a computer system upon which one or more examples may be implemented.

FIG. 2 illustrates a flow diagram of an example process for candidate screening for a target therapy. Process 200 may be performed by one or more computing devices and/or processes thereof. For example, one or more blocks of process 200 may be performed by a computer system, such as but not limited to computer system 400. Process 200 will be described with respect to the target therapy analysis system 120 of FIG. 1, but is not limited to performance by such.

At block 202, the target therapy analysis system 120 identifies a plurality of medical codes corresponding to patient billing data.

At block 204, the target therapy analysis system 120 generates a candidate classification model for a target therapy by selecting a set of medical codes from the plurality of medical codes and assigning a weight to each medical code selected. In some examples, the target therapy is a left atrial appendage (LAA) occlusion comprising an LAA occluder implantation procedure. In some examples, the target therapy analysis system 120 provides a user interface for adjusting one or more weights assigned to one or more medical codes of the set of medical codes. In some examples, generating the candidate classification model for the target therapy includes assigning one or more negative weights to one or more medical codes corresponding to one or more exclusion criteria for the target therapy, and assigning one or more positive weights to one or more medical codes corresponding to one or more inclusion criteria for the target therapy. As an alternative or addition, generating the candidate classification model includes grouping two or more medical codes in the set of medical codes into a code group, and assigning a single weight to the code group to indirectly assign weights to the two or more medical codes of the code group. As an alternative or addition, generating the candidate classification model includes use machine learning techniques to assign one or more weights of the candidate classification model based on a training data set comprising input data that includes associations between medical codes and a plurality of sample patients, and output data that includes a sample target therapy score for each sample patient.

At block 206, the target therapy analysis system 120 receives patient billing data for a plurality of patients. The patient billing data includes associations between one or more patients of the plurality of patients and one or more medical codes of the plurality of medical codes. In some examples, the patient billing data is received from a medical organization. The patient billing data may be received in a deidentified form.

At block 208, the target therapy analysis system 120 applies the candidate classification model to the patient billing data to generate a set of target therapy scores. Each target therapy score of the set of target therapy scores corresponds to a patient of the plurality of patients. Each target therapy score is calculated based on weights for one or more medical codes associated with the corresponding patient.

At block 210, the target therapy analysis system 120 provides target therapy candidate data generated based on the set of target therapy scores. For example, the target therapy candidate data may be provided to a medical organization, such as a medical organization from which the patient billing data was received. The target therapy candidate data may reference individual patients in the plurality of patients by pseudonym.

In some examples, providing the target therapy candidate data includes providing at least a subset of the set of target therapy scores. As an alternative or addition, the target therapy candidate data may identify one or more candidate patients having a target therapy score that meets a target therapy score threshold. As an alternative or addition, the target therapy candidate data may include an individual report for at least one patient of the plurality of patients. As an alternative or addition, the target therapy candidate data may include aggregate data for one or more target therapy classifications over one or more groupings of the plurality of patients.

Figure 3:
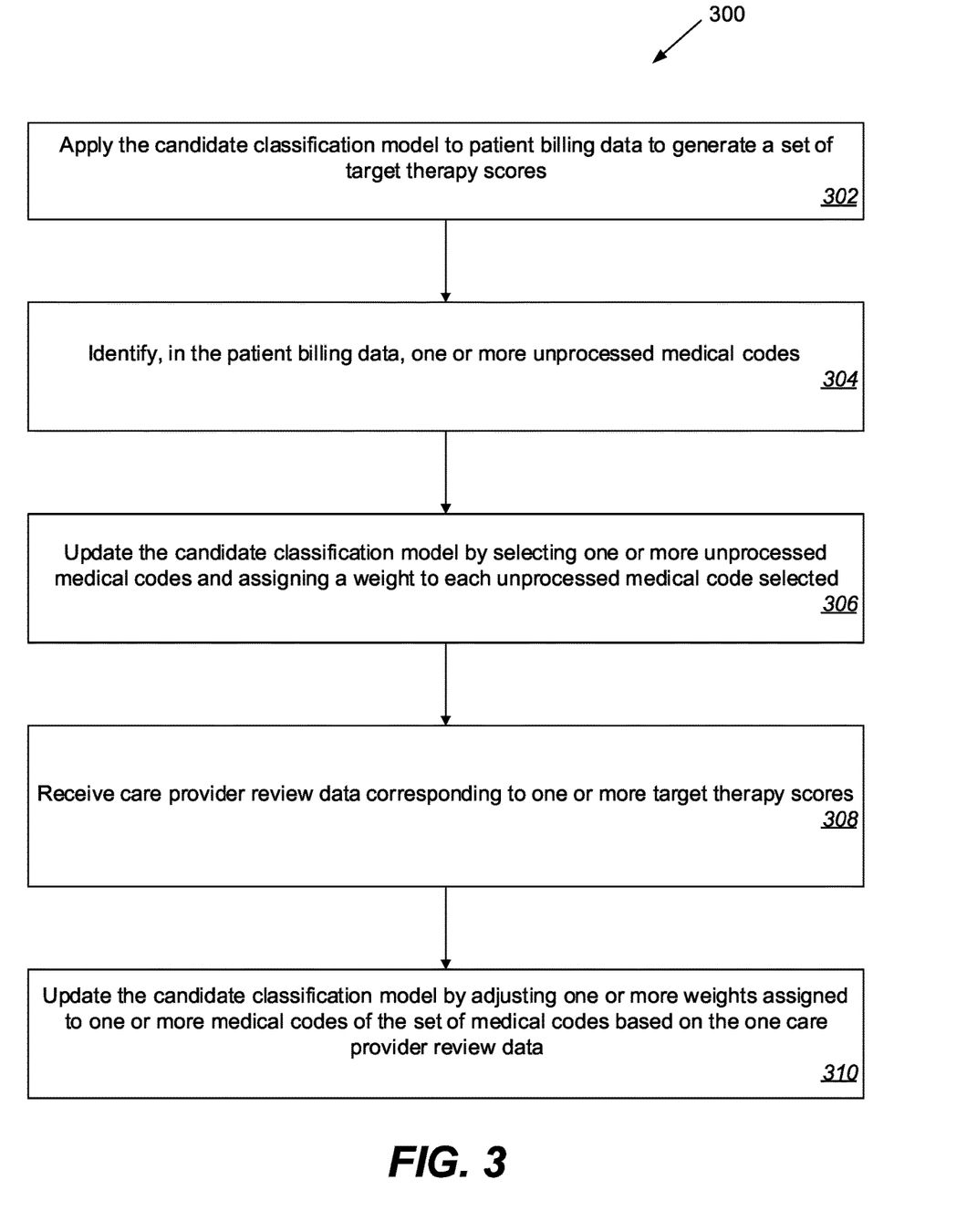
FIG. 3 illustrates a flow diagram of an example process for updating a candidate classification model for a target therapy.

FIG. 3 illustrates a flow diagram of an example process for updating a candidate classification model for a target therapy. Process 300 may be performed by one or more computing devices and/or processes thereof. For example, one or more blocks of process 300 may be performed by a computer system, such as but not limited to computer system 400. Process 300 will be described with respect to the target therapy analysis system 120 of FIG. 1, but is not limited to performance by such.

At block 302, the target therapy analysis system 120 applies the candidate classification model to patient billing data to generate a set of target therapy scores.

At block 304, the target therapy analysis system 120 identifies, in the patient billing data, one or more unprocessed medical codes not in the plurality of medical codes.

At block 306, the target therapy analysis system 120 updates the candidate classification model by selecting one or more unprocessed medical codes from the one or more unprocessed medical codes and assigning a weight to each unprocessed medical code selected.

At block 308, the target therapy analysis system 120 receives care provider review data corresponding to one or more target therapy scores of the set of target therapy scores.

At block 310, the target therapy analysis system 120 updates the candidate classification model by adjusting one or more weights assigned to one or more medical codes of the set of medical codes based on the care provider review data.

Implementation Mechanisms—Hardware Overview

The techniques described herein may be implemented by one or more special-purpose computing devices. The special-purpose computing devices may be hard-wired to perform one or more techniques described herein, including combinations thereof. Alternatively and/or in addition, the one or more special-purpose computing devices may include digital electronic devices such as one or more application-specific integrated circuits (ASICs) or field-programmable gate arrays (FPGAs) that are persistently programmed to perform the techniques. Alternatively and/or in addition, the one or more special-purpose computing devices may include one or more general-purpose hardware processors programmed to perform the techniques described herein pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices, and/or any other device that incorporates hard-wired or program logic to implement the techniques.

FIG. 4 is a block diagram that illustrates a computer system upon which an example may be implemented. The computer system 400 includes a bus 402 or other communication mechanism for communicating information, and one or more hardware processors 404 coupled with bus 402 for processing information, such as computer instructions and data. The processor/s 404 may include one or more general-purpose microprocessors, graphical processing units (GPUs), coprocessors, central processing units (CPUs), and/or other hardware processing units.

The computer system 400 also includes one or more units of main memory 406 coupled to the bus 402, such as random-access memory (RAM) or other dynamic storage, for storing information and instructions to be executed by the processor/s 404. Main memory 406 may also be used for storing temporary variables or other intermediate information during execution of instructions to be executed by the processor/s 404. Such instructions, when stored in non-transitory storage media accessible to the processor/s 404, turn the computer system 400 into a special-purpose machine that is customized to perform the operations specified in the instructions. In some embodiments, main memory 406 may include dynamic random-access memory (DRAM) (including but not limited to double data rate synchronous dynamic random-access memory (DDR SDRAM), thyristor random-access memory (T-RAM), zero-capacitor (Z-RAM™)) and/or non-volatile random-access memory (NVRAM).

The computer system 400 may further include one or more units of read-only memory (ROM) 408 or other static storage coupled to the bus 402 for storing information and instructions for the processor/s 404 that are either always static or static in normal operation but reprogrammable. For example, the ROM 408 may store firmware for the computer system 400. The ROM 408 may include mask ROM (MROM) or other hard-wired ROM storing purely static information, programmable read-only memory (PROM), erasable programmable read-only memory (EPROM), electrically-erasable programmable read-only memory (EEPROM), another hardware memory chip or cartridge, or any other read-only memory unit.

One or more storage devices 410, such as a magnetic disk or optical disk, is provided and coupled to the bus 402 for storing information and/or instructions. The storage device/s 410 may include non-volatile storage media such as, for example, read-only memory, optical disks (such as but not limited to compact discs (CDs), digital video discs (DVDs), Blu-ray discs (BDs)), magnetic disks, other magnetic media such as floppy disks and magnetic tape, solid-state drives, flash memory, optical disks, one or more forms of non-volatile random-access memory (NVRAM), and/or other non-volatile storage media.

The computer system 400 may be coupled via the bus 402 to one or more input/output (I/O) devices 412. For example, the I/O device/s 412 may include one or more displays for displaying information to a computer user, such as a cathode ray tube (CRT) display, a Liquid Crystal Display (LCD) display, a Light-Emitting Diode (LED) display, a projector, and/or any other type of display.

The I/O device/s 412 may also include one or more input devices, such as an alphanumeric keyboard and/or any other keypad device. The one or more input devices may also include one or more cursor control devices, such as a mouse, a trackball, a touch input device, or cursor direction keys for communicating direction information and command selections to the processor 404 and for controlling cursor movement on another I/O device (e.g. a display). A cursor control device typically has degrees of freedom in two or more axes, (e.g. a first axis x, a second axis y, and optionally one or more additional axes z), that allows the device to specify positions in a plane. In some embodiments, the one or more I/O device/s 412 may include a device with combined I/O functionality, such as a touch-enabled display.

Other I/O device/s 412 may include a fingerprint reader, a scanner, an infrared (IR) device, an imaging device such as a camera or video recording device, a microphone, a speaker, an ambient light sensor, a pressure sensor, an accelerometer, a gyroscope, a magnetometer, another motion sensor, or any other device that can communicate signals, commands, and/or other information with the processor/s 404 over the bus 402.

The computer system 400 may implement the techniques described herein using customized hard-wired logic, one or more ASICs or FPGAs, firmware, and/or program logic which, in combination with the computer system causes or programs, causes computer system 400 to be a special-purpose machine. In some examples, the techniques herein are performed by the computer system 400 in response to the processor/s 404 executing one or more sequences of one or more instructions contained in main memory 406. Such instructions may be read into main memory 406 from another storage medium, such as the one or more storage device/s 410. Execution of the sequences of instructions contained in main memory 406 causes the processor/s 404 to perform the process steps described herein. In alternative embodiments, hard-wired circuitry may be used in place of or in combination with software instructions.

The computer system 400 also includes one or more communication interfaces 418 coupled to the bus 402. The communication interface/s 418 provide two-way data communication over one or more physical or wireless network links 420 that are connected to a local network 422 and/or a wide area network (WAN), such as the Internet. For example, the communication interface/s 418 may include an integrated services digital network (ISDN) card, cable modem, satellite modem, or a modem to provide a data communication connection to a corresponding type of telephone line. Alternatively and/or in addition, the communication interface/s 418 may include one or more of: a local area network (LAN) device that provides a data communication connection to a compatible local network 422; a wireless local area network (WLAN) device that sends and receives wireless signals (such as electrical signals, electromagnetic signals, optical signals or other wireless signals representing various types of information) to a compatible LAN; a wireless wide area network (WWAN) device that sends and receives such signals over a cellular network; and other networking devices that establish a communication channel between the computer system 400 and one or more LANs 422 and/or WANs.

The network link/s 420 typically provides data communication through one or more networks to other data devices. For example, the network link/s 420 may provide a connection through one or more local area networks 422 (LANs) to one or more host computers 424 or to data equipment operated by an Internet Service Provider (ISP) 426. The ISP 426 provides connectivity to one or more wide area networks 428, such as the Internet. The LAN/s 422 and WAN/s 428 use electrical, electromagnetic, or optical signals that carry digital data streams. The signals through the various networks and the signals on the network link/s 420 and through the communication interface/s 418 are example forms of transmission media, or transitory media.

The term "storage media" as used herein refers to any non-transitory media that stores data and/or instructions that cause a machine to operate in a specific fashion. Such storage media may include volatile and/or non-volatile media. Storage media is distinct from but may be used in conjunction with transmission media. Transmission media participates in transferring information between storage media. For example, transmission media includes coaxial cables, copper wire and fiber optics, including traces and/or other physical electrically conductive components that comprise the bus 402. Transmission media can also take the form of acoustic or light waves, such as those generated during radio-wave and infra-red data communications.

Various forms of media may be involved in carrying one or more sequences of one or more instructions to the processor 404 for execution. For example, the instructions may initially be carried on a magnetic disk or solid-state drive of a remote computer. The remote computer can load the instructions into its main memory 406 and send the instructions over a telecommunications line using a modem. A modem local to the computer system 400 can receive the data on the telephone line and use an infra-red transmitter to convert the data to an infra-red signal. An infra-red detector can receive the data carried in the infra-red signal and appropriate circuitry can place the data on the bus 402. The bus 402 carries the data to main memory 406, from which the processor 404 retrieves and executes the instructions. The instructions received by main memory 406 may optionally be stored on the storage device 410 either before or after execution by the processor 404.

The computer system 400 can send messages and receive data, including program code, through the network(s), the network link 420, and the communication interface/s 418. In the Internet example, one or more servers 430 may transmit signals corresponding to data or instructions requested for an application program executed by the computer system 400 through the Internet 428, ISP 426, local network 422 and a communication interface 418. The received signals may include instructions and/or information for execution and/or processing by the processor/s 404. The processor/s 404 may execute and/or process the instructions and/or information upon receiving the signals by accessing main memory 406, or at a later time by storing them and then accessing them from the storage device/s 410.

OTHER ASPECTS OF DISCLOSURE

Although the concepts herein have been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. A method comprising:
  performing, by one or more processors, the steps of:
    identifying a plurality of medical codes corresponding to patient billing data, the plurality of medical codes including a first medical code corresponding to a risk for bleeding and a second medical code corresponding to existence of atrial fibrillation;
    generating a candidate classification model for a target therapy by selecting a set of medical codes from the plurality of medical codes and assigning a weight to each medical code selected, the target therapy being a left atrial appendage ("LAA") occlusion therapy;
    receiving patient billing data for a plurality of patients, the patient billing data including associations between one or more patients of the plurality of patients and one or more medical codes of the plurality of medical codes;
    applying the candidate classification model to the patient billing data to generate a set of target therapy scores, each target therapy score of the set of target therapy scores corresponding to a patient of the plurality of patients and calculated based on weights for one or more medical codes associated with the patient, wherein the set of target therapy scores includes (i) a first score indicating that the corresponding patient has previously received the LAA occlusion therapy, (ii) a second score indicating that the corresponding patient is at a high risk of stroke, and (iii) a third score indicating that the corresponding patient is not at a high risk of stroke; and providing target therapy candidate data generated based on the set of target therapy scores;

based on the provided target therapy candidate data, identifying a selected patient from the plurality of patients, the target therapy score corresponding to the selected patient being the second score indicating that the selected patient is at the high risk of stroke; and after identifying the selected patient, implanting a LAA occluder into the LAA of the selected patient to occlude the LAA of the selected patient.

2. The method of claim 1, wherein the target therapy candidate data identifies one or more candidate patients having a target therapy score that meets a target therapy score threshold.

3. The method of claim 1, wherein the target therapy candidate data includes an individual report for at least one patient of the plurality of patients.

4. The method of claim 1, wherein the target therapy candidate data includes aggregate data for one or more target therapy classifications over one or more groupings of the plurality of patients.

5. The method of claim 1, wherein generating the candidate classification model for the target therapy includes:

assigning one or more negative weights to one or more medical codes corresponding to one or more exclusion criteria for the target therapy; and assigning one or more positive weights to one or more medical codes corresponding to one or more inclusion criteria for the target therapy.

6. The method of claim 1, wherein generating the candidate classification model includes:

grouping two or more medical codes in the set of medical codes into a code group; and assigning a single weight to the code group to indirectly assign weights to the two or more medical codes of the code group.

7. The method of claim 1, wherein receiving the patient billing data includes receiving the patient billing data from a medical organization;

wherein providing the target therapy candidate data set comprises providing the set of target therapy scores to the medical organization;

wherein the patient billing data is received from the medical organization in a deidentified form; and wherein the target therapy candidate data references individual patients in the plurality of patients by pseudonym.

8. The method of claim 1, wherein generating the candidate classification model includes use of machine learning techniques to assign one or more weights of the candidate classification model based on a training data set comprising:

input data comprising associations between medical codes and a plurality of sample patients; and output data comprising a sample target therapy score for each sample patient of the plurality of sample patients.

9. The method of claim 1, further comprising:

receiving care provider review data corresponding to one or more target therapy scores of the set of target therapy scores; and updating the candidate classification model by adjusting one or more weights assigned to the one or more medical codes of the set of medical codes based on the care provider review data.

\* \* \* \* \*